(12) United States Patent
Hodgetts et al.

(10) Patent No.: US 6,403,591 B1
(45) Date of Patent: Jun. 11, 2002

(54) 1-AZATRICYCLIC-4-BENZYLPIPERAZINES

(75) Inventors: Kevin Hodgetts; Stanislaw Rachwal; Daniel Rosewater, all of Branford; Andrew Thurkauf, Danbury; Xiaoyan Zhang, East Haven, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/894,092

(22) Filed: Jun. 28, 2001

Related U.S. Application Data

(63) Continuation of application No. 09/596,020, filed on Jun. 14, 2000, now Pat. No. 6,294,530.
(60) Provisional application No. 60/139,135, filed on Jun. 14, 1999.

(51) Int. Cl.[7] .............................................. A61K 31/497
(52) U.S. Cl. ............................ 514/253.08; 514/253.09; 544/361; 544/373
(58) Field of Search ................................. 544/373, 361; 514/253.08, 254.09

(56) References Cited

FOREIGN PATENT DOCUMENTS

EP        655 451        * 5/1995

\* cited by examiner

*Primary Examiner*—Bruck Kifle
(74) *Attorney, Agent, or Firm*—McDonnell Boehnen Hulbert & Berghoff

(57) ABSTRACT

Disclosed are 1-Azatricyclic-4-benzylpiperazine compounds which are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents. Pharmaceutical compositions, including packaged pharmaceutical compositions, are further provided. Compounds of the invention are also useful as probes for the localization of $GABA_A$ receptors in tissue samples.

10 Claims, No Drawings

1-AZATRICYCLIC-4-BENZYLPIPERAZINES

This is a continuation of application Ser. No. 09/596,020 now U.S. Pat. No. 6,294,530, filed Jun. 14, 2000, which claims priority from application Ser. No. 60/139,135, filed Jun. 14, 1999.

BACKGROUND OF THE INVENTION

1. Field of the Invention

This invention relates to 1-azatricyclic-4-benzylpiperazines, and to compounds that bind to dopamine receptors. This invention also relates to pharmaceutical compositions comprising such compounds and also to the treatment of central nervous system (CNS) diseases, particularly the treatment or prevention of psychotic disorders such as to schizophrenia. Additionally this invention relates to the use of compounds as probes for the localization of dopamine receptors in tissue sections.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has been identified and cloned. Its unique localization in limbic brain areas and its differential recognition of various antipsychotics suggest that the $D_4$ receptor may play a major role in the etiology of schizophrenia. The dopamine $D_4$ receptor shares sequence homology with dopamine $D_2$ and $D_3$ receptors, however the $D_4$ receptor possesses a unique pharmacological profile. Selective $D_4$ antagonists, including the marketed antipsychotic chlozapine, are considered effective antipsychotics free from the neurological side effects displayed by conventional neuroleptics. Compounds that possess a 10-fold or more higher affinity for dopamine $D_4$ receptors than $D_2$ receptors are considered particularly desirable as antipsychotics.

Since dopamine $D_4$ receptors are concentrated in the limbic system which controls cognition and emotion, compounds which interact with these receptors have utility in the treatment of cognitive disorders. Such disorders include the cognitive deficits which are a significant component of the negative symptoms (social withdrawal and unresponsiveness) of schizophrenia. Other disorders involving memory impairment or attention deficit disorder can also be treated with compound that interact specifically with the dopamine $D_4$ receptor subtype.

SUMMARY OF THE INVENTION

This invention provides 1-azatricyclic-4-benzylpiperazine compounds that bind, preferably with high affinity and selectivity, to the $D_4$ receptor subtype, including human $D_4$ receptors. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Thus, the invention provides compounds of Formula I (shown below), and pharmaceutical compositions comprising compounds of Formula I.

The invention further comprises methods of treating patients suffering from CNS disorder with a therapeutically effective amount of a compound of the invention. The patient may be a human or other mammal. Treatment of humans, domesticated companion animals (pets) or livestock animals suffering from CNS disorder with a therapeutically effective amount of a compound of the invention is encompassed by the invention. Particularly methods for the treatment and/or prevention of neuropsychological or affective disorders, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents are included. In addition, the compounds of the invention are useful in treatment of depression, memory-impairment or Alzheimer's disease by modulation of $D_4$ receptors which selectively exist in limbic areas known to control emotion and cognitive functions. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

Accordingly, a broad aspect of the invention is directed to compounds of Formula I:

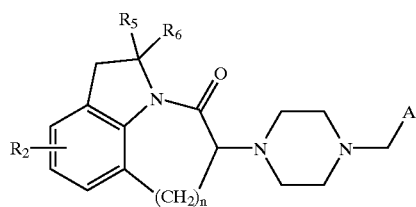

I or a pharmaceutically acceptable salt thereof, wherein

A represents phenyl optionally substituted with up to four groups independently selected from halogen, hydroxy, amino, mono- or di($C_1$–$C_6$)hydrocarbylamino, aminosulfonyl, $C_1$–$C_6$ hydrocarbylaminosulfonyl, di($C_1$–$C_6$)hydrocarbylaminosulfonyl, cyano, nitro, cyclohydrocarbylhydrocarbyl, trifluoromethyl, $C_1$–$C_6$ hydrocarbyl, trifluoromethoxy, $C_3$–$C_6$ cyclohydrocarbyl, and $C_1$–$C_6$ alkoxy;

$R_5$ and $R_6$ are the same or different and represent hydrogen or $C_1$–$C_6$ hydrocarbyl; and $R_2$ represents hydrogen, halogen, hydroxy, amino, mono- or di($C_1$–$C_6$)hydrocarbylamino, aminosulfonyl, $C_1$–$C_6$ hydrocarbylaminosulfonyl, di($C_1$–$C_6$) hydrocarbylaminosulfonyl, cyano, nitro, cyclohydrocarbylhydrocarbyl, trifluoromethyl, $C_1$–$C_6$ hydrocarbyl, trifluoromethoxy, $C_3$–$C_6$ cyclohydrocarbyl, or $C_1$–$C_6$ alkoxy; and n is 0, 1, or 2.

DETAILED DESCRIPTION OF THE INVENTION

The invention encompasses the compounds of Formula I described above.

In preferred compounds of formula I,

A represents phenyl optionally substituted with up to four groups independently selected from halogen, hydroxy, amino, mono- or di($C_1$–$C_6$)alkylamino, aminosulfonyl $C_1$–$C_6$ alkylaminosulfonyl, di ($C_1$–$C_6$) alkylaminosulfonyl, cyano, nitro, cycloalkylalkyl, trifluoromethyl, ($C_1$–$C_6$) alkyl, trifluoromethoxy, $C_3$–$C_6$ cycloalkyl, and $C_1$–$C_6$ alkoxy;

$R_5$ and $R_6$ are the same or different and represent hydrogen or $C_1$–$C_6$ alkyl; and $R_2$ represents hydrogen, halogen, hydroxy, amino, mono- or di($C_1$–$C_6$)alkylamino, aminosulfonyl, $C_1$–C6 alkylaminosulfonyl, di($C_1$–$C_6$)alkylaminosulfonyl, cyano, nitro, cycloalkylalkyl, trifluoromethyl, ($C_1$–$C_6$) alkyl, trifluoromethoxy, $C_3$–$C_6$ cycloalkyl, or $C_1$–$C_6$ alkoxy; and n is 0, 1, or 2.

In other preferred compounds of Formula I, n is 2;

A represents phenyl optionally substituted with up to four groups independently selected from halogen, hydroxy, amino, mono- or di($C_1$–$C_6$) alkylamino, cyano, nitro, cycloalkylalkyl, trifluoromethyl, ($C_1$–$C_6$)alkyl, trifluoromethoxy, $C_3$–$C_6$ cycloalkyl, and $C_1$–$C_6$ alkoxy;

$R_5$ and $R_6$ are the same or different and represent hydrogen or $C_1$–$C_6$ alkyl; and $R_2$ represents hydrogen, halogen, hydroxy, amino, mono- or di ($C_1$–$C_6$) alkylamino, cyano, nitro, cycloalkylalkyl, trifluoromethyl, ($C_1$–$C_6$)alkyl, trifluoromethoxy, $C_3$–$C_6$ cycloalkyl, or $C_1$–$C_6$ alkoxy.

More preferred compounds of Formula I are those where A is a group of the formula:

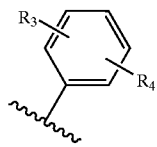

where $R_3$ and $R_4$ independently represent hydrogen, halogen, hydroxy, amino, aminosulfonyl, $C_1$–$C_6$ alkylaminosulfonyl, di($C_1$–$C_6$)alkylaminosulfonyl, cyano, nitro, trifluoromethoxy, $C_1$–$C_6$ alkyl, or $C_1$–$C_6$ alkoxy.

These more preferred compounds are represented by Formula II herein.

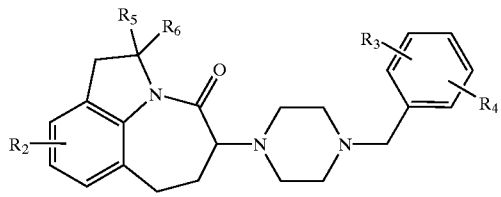

In preferred compounds of Formula II, $R_3$ and $R_4$ are the same or different and are $C_1$–$C_3$ alkyl, chloro, fluoro, bromo, or $C_1$–$C_3$ alkoxy. More preferably, in compounds of Formula II at least one of $R_3$ and $R_4$ is attached at the ortho or para position of the phenyl ring. Still more preferably, $R_2$ in Formula II is hydrogen, fluoro, chloro, or $C_1$–$C_2$ alkyl.

In other preferred compounds of II, $R_2$ is hydrogen. Such compounds are designated as compounds of Formula II-A hereinafter. In these compounds, $R_3$ and $R_4$ are the same or different and are $C_1$–$C_3$ alkyl, chloro, fluoro, bromo, or $C_1$–$C_3$ alkoxy. Preferably compounds of Formula II-A are those where at least one of $R_3$ and $R_4$ is in the ortho or para position of the phenyl ring. More preferred compounds of II-A are those wherein $R_5$ and $R_6$ independently represent hydrogen or $C_1$–$C_2$ alkyl. Still other more preferred compounds of II-A are those wherein at least one of $R_5$ and $R_6$ is methyl. Particularly preferred compounds of II-A are those where both $R_5$ and $R_6$ are methyl. Other particularly preferred compounds of Formula II-A are those where $R_5$ is methyl and $R_6$ is hydrogen.

The compounds of this invention may contain one or more asymmetric centers, e.g., carbon atoms, so that the compounds can exist in different stereoisomeric forms. These compounds can be, for example, mixtures of diastereomers, or racemates or resolved enantiomers. Single enantiomers can be obtained as pure compounds or in enantiomeric excess by asymmetric synthesis or by resolution of the racemate. Resolution of the racemate can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include, but are not limited to salts of inorganic acids such as hydrochloric, sulfuric, phosphoric, diphosphoric, hydrobromic, and nitric or salts of organic acids such as formaic, citric, malic, maleic, fumaric, tartanic, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts.

The present invention also encompasses prodrugs of the compounds of Formula I, e.g., acylated compounds and esters of Formula I. Those skilled in the art will recognize various synthetic methodologies which may be employed to prepare non-toxic pharmaceutically acceptable addition salts and prodrugs of the compounds encompassed by Formula I.

Where a compound exists in various tautomeric forms, the invention is not limited to any one of the specific tautomers. The invention includes all tautomeric forms of a compound.

Representative compounds of the invention are shown below in Table 1.

TABLE 1

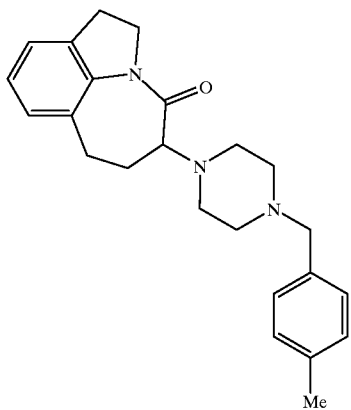

Compound 1

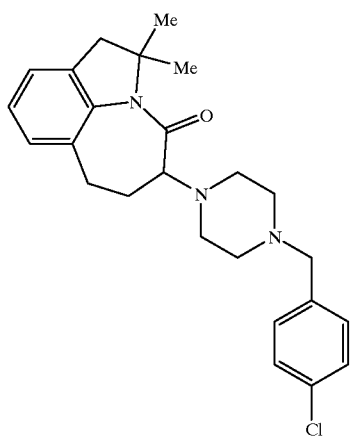

Compound 2

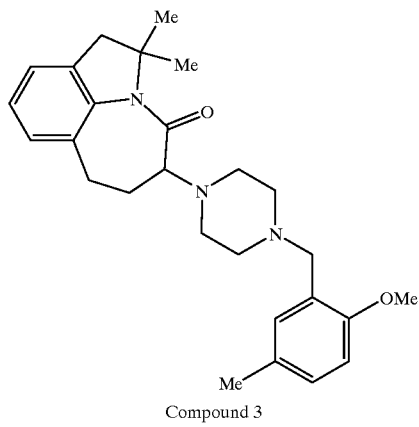

Compound 3

TABLE 1-continued

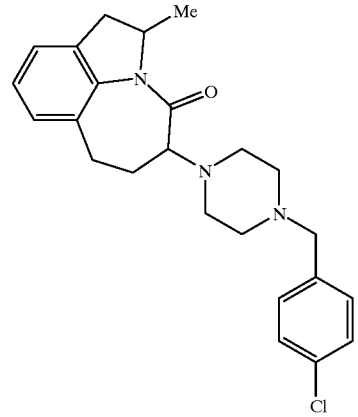

Compound 4

This invention provides 1-azatricyclic-4-benzylpiperazine compounds that bind with high affinity to dopamine receptors, particularly dopamine $D_4$ receptors, including human dopamine $D_4$ receptors. This invention also includes compounds that bind with high selectivity to dopamine receptors, particularly dopamine $D_4$ receptors, including human dopamine $D_4$ receptors. Without wishing to be bound to any particular theory, it is believed that the interaction of the compounds of the invention with the dopamine $D_4$ receptor results in the pharmaceutical utility of these compounds.

The invention further comprises methods of treating patients suffering from a CNS disorder with an amount of a compound of the invention sufficient to alter the symptoms of the disorder.

The diseases, conditions and disorders that can be treated using compounds and compositions according to the invention include, but are not limited to, schizophrenia, psychotic depression, mania, and the extrapyramidyl side effects associated with the use of a neuroleptic agent. Other dopamine-mediated disease such as Parkinsonism and tardive dyskinesias can also be treat directly or indirectly by modulation of dopamine receptors. Compounds of the invention are also useful in the treatment of depression, memory-impairment or Alzheimer's disease by modulation of $D_4$ receptors since these receptors are localized in areas known to control emotion and cognitive functions.

The invention also provides pharmaceutical compositions comprising compounds of the invention, including packaged pharmaceutical compositions, for treating disorders responsive to dopamine receptor modulation, especially dopamine $D_4$ receptor modulation, e.g., treatment of schizophrenia, depression, tardive diskinesia or cognitive impairment by dopamine $D_4$ receptor modulation. The packaged pharmaceutical compositions include a container holding a define quantity or unit dose, e.g., a therapeutically effective amount, of at least one compound of the invention and instructions (e.g., labeling) indicating how the contained compound is to be used in the patient, e.g., for treating a disorder responsive to dopamine receptor modulation.

The present invention also pertains to methods of inhibiting the binding of dopamine to dopamine $D_4$ receptors which methods involve contacting a compound of the invention with cells expressing dopamine $D_4$ receptors, wherein the compound is present at a concentration sufficient to inhibit dopamine binding to dopamine $D_4$ receptors in vitro. This method includes inhibiting the binding of dopamine to dopamine $D_4$ receptors in vivo, e.g., in a patient given an amount of a compound of Formula I that would be sufficient to inhibit the binding of dopamine to dopamine $D_4$ receptors in vitro. The amount of a compound that would be sufficient to inhibit the binding of dopamine to the dopamine $D_4$ receptor may be readily determined via a dopamine receptor binding assay, such as the assay described in Example 3. The dopamine receptors used to determine in vitro binding may be obtained from a variety of sources, for example from preparations of rat striatal homogenates or from cells expressing cloned human or monkey dopamine $D_4$ receptors.

The compounds of this invention and labeled derivatives thereof are also useful as standards and reagents in determining the ability of a potential pharmaceutical agent to bind to the dopamine $D_4$ receptor.

Radiolabeled derivatives of the compounds of this invention are also useful as radiotracers for positron emission tomography (PET) imaging or for single photon emission computerized tomography (SPECT).

Definitions

Where the compounds of the present invention have asymmetric centers, the invention includes all of the optical isomers and mixtures thereof.

Compounds with carbon-carbon double bonds may occur in Z- and E-forms, and all the isomers of such compounds are included in the invention.

When any variable (e.g. $C_{1-6}$ alkyl, $C_{1-8}$ alkyl, A, $R_2$, $R_5$, or $R_6$) occurs more than one time in any formula herein, its definition at each occurrence is independent of its definition at every other occurrence.

By "$C_1$–$C_6$ alkyln" in the present invention is meant straight or branched chain alkyl groups having 1–6 carbon atoms. Examples of alkyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "$C_1$–$C_6$ hydrocarbyl" in the present invention is meant straight or branched chain alkyl groups having 1–6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, and propargyl. When reference is made herein to $C_1$–$C_6$ hydrocarbyl containing one or two double or triple bonds it is understood that at least two carbons are present in the alkyl for one double or triple bond, and at least four carbons for two double or triple bonds.

By "$C_1$–$C_6$ alkoxy" or "lower alkoxy" in the present invention is meant an alkyl group of indicated number of carbon atoms attached to the parent molecular moiety through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. Preferred alkoxy groups herein are $C_1$–$C_4$ alkoxy groups.

The term "cycloalkylalkyl," as used herein, refers to a $C_3$–$C_7$ cycloalkyl group attached to the parent molecular moiety through an alkyl group, as defined above. Examples of cycloalkylalkyl groups include cyclopropylmethyl and cyclopentylethyl.

The term "halogen" indicates fluorine, chlorine, bromine, or iodine.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the compounds of Formula I may be added to the animals feed or drinking water. It will be convenient to formulate these animal feed and a drinking water compositions so that the animal consumes an appropriate quantity, e.g., a therapeutically effective amount, of the compound in its diet. It will also be convenient to in present the compound in a composition as a premix for addition to the feed or drinking water.

Dosage levels of the order of from about 0.1 mg to about 140 mg per kilogram of body weight per day are useful in the treatment of the above-indicated conditions (about 0.5 mg to in about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of schizophrenia, depression, or cognitive impairment a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

Preparation of Compounds

A representative synthesis of the compounds of the invention is presented in Scheme I. Those having skill in the art will recognize that the starting materials and reaction conditions may be varied and additional steps employed to produce compounds encompassed by the present invention, as demonstrated by the following examples. In some cases, protection of reactive functionalities may be necessary to achieve some of the transformations. In general, the need for such protecting groups as well as the conditions necessary to attach and remove such groups will be apparent to those skilled in the art of organic synthesis.

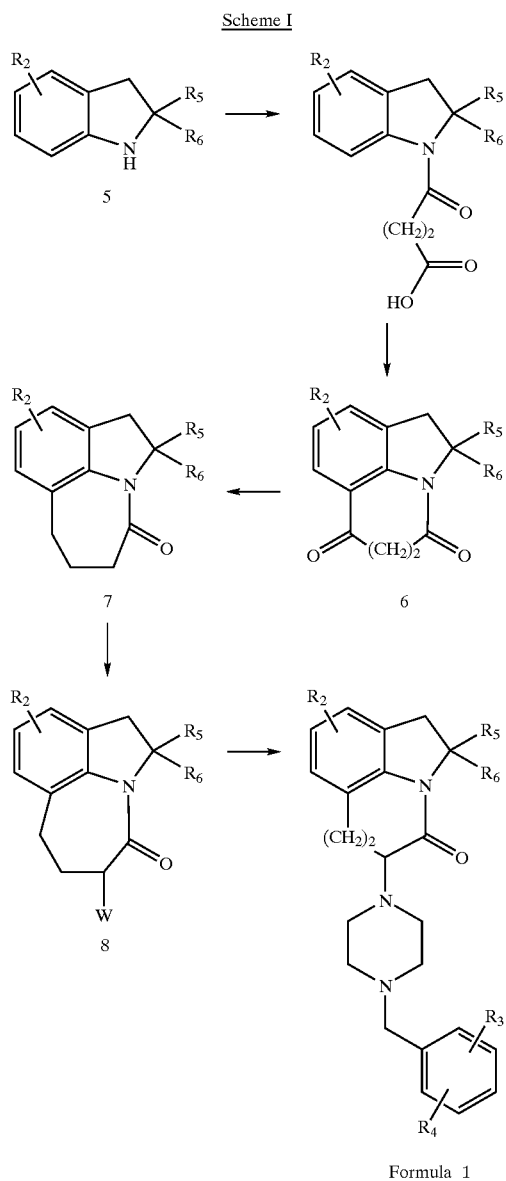

Scheme I

Formula 1

In Scheme I, $R_2$, $R_3$, $R_4$, $R_5$ and $R_6$ are as defined for Formula I. W is appropriate leaving group such as, for example, halogen or a sulfonate ester.

The starting indolines (5) are either commercially available, known, or capable of being prepared by the methods known in the art. Thus, to prepare compounds where $R_5$ and $R_6$ are alkyl, starting indoline (5) may be prepared by the methods of Azadi-Ardakani (*J. Chem. Soc. Perkin Trans* I. 1986, 1107). Azatricyclics 6 and 7 may be prepared according to the methods of Bass et al (*J. Agri. Food Chem.* 1981, 29, 576) or DeLombaert (*Bioorg. Med. Chem. Lett.* 1994, 7513). Preparation of intermediates containing an iodo leaving group (i.e., 8, where W=iodine) may be carried out by the method of Fisher (PCT application WO 95/16692). Other compounds may be prepared by procedures analogous to those described in literature.

The disclosures in this application of all articles and references, including patents, are incorporated herein by reference in their entirety.

The invention is further illustrated by the following examples which are not to be construed as limiting the invention in scope or spirit to the specific procedures described in them.

EXAMPLES

Example 1

The following scheme represents the synthesis described below.

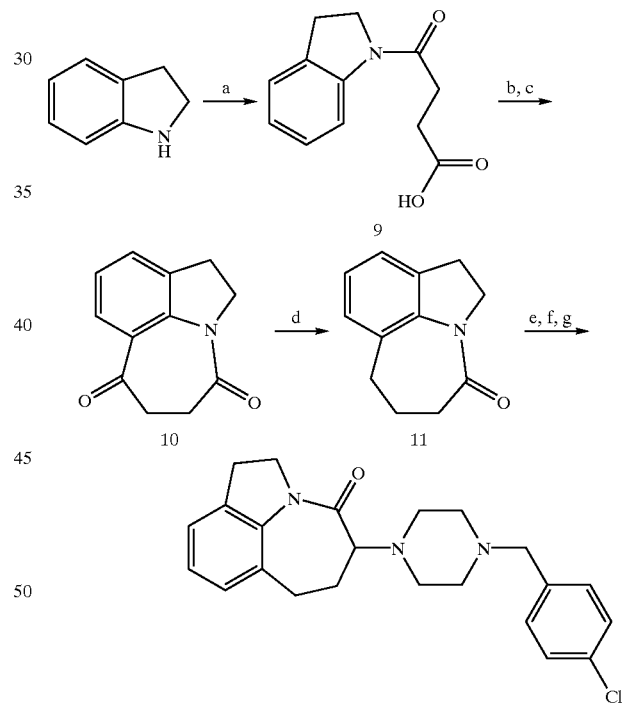

a. succinic anhydride, Et$_3$N, CHCl$_3$; b. (COCl)$_2$, DMF (cat), DCE; c. AlCl$_3$;
d. H$_2$ (50 psi), AcOH, Pd/C; e. TMEDA, TMSI, $_2$Cl$_2$, 0° C.; f. I$_2$, 0° C.;
g. p-Chlorobenzylpiperizine, K$_2$CO$_3$, CH$_3$CN, reflux.

Compound 9. Indoline (23.8 g, 0.2 mol), succinic anhydride (20.0 g, 0.2 mol) and triethylamine (40 mL) are combined in chloroform (200 mL) and stirred at room temperature for about sixteen hours. The solvent is then removed under reduced pressure and the product is precipitated by adding aqueous HCl solution (5%, 500 mL). After filtration, the filter cake is washed with water and dried to give compound 9 (35.2 g, 80%) as an off-white powder: $^1$H NMR (300 MHz, CDCl₃) 2.76–2.81 (m, 4H), 3.23 (t, J=8.1 Hz, 2H), 4.09 (t, J=8.1 Hz, 2H), 7.04 (t, J=6.9 Hz, 1H), 7.18–7.22 (m, 2H), 8.20 (d, J=8.4 Hz, 1H); MS (LC-MS) m/e 202 (M+H−18)₊.

Compound 10. To a solution of compound 9 (15.0 g, 0.068 mol) in dichloroethane (250 mL) is added dimethylformamide (0.5 mL) and oxalyl chloride (8 mL, 0.092 mol). The resulting solution is stirred for about 1 h at room temperature, and then cooled to 0° C. with an ice bath. A suspension of aluminum trichloride (36.5 g, 0.27 mol) in dichloroethane (100 mL) is poured into the reaction mixture. The ice bath is removed and the reaction mixture is heated to 50° C. for about 4 h. Additional aluminum trichloride (9.0 g, 0.068 mol) is added and the heating is continued overnight. The reaction mixture is cooled to room temperature and then poured on to ice. The resulting slurry is filtered and the product extracted several times with dichloromethane. The combined dichloromethane extracts are dried over sodium sulfate, filtered and concentrated. The crude product is purified by chromatography on silica gel, eluting with 50% ethyl acetate in hexanes to yield 2.5 g (18%) of compound 10 as a light yellow powder. ¹H NMR (300 MHz, CDCl₃) 2.84–2.88 (m, 2H), 2.92–2.96 (m, 2H), 3.16 (t, J=8.7 Hz, 2H), 4.25 (t, J=8.7 Hz, 2H), 7.11 (t, J=7.8 Hz, 1H), 7.42 (dd, J=1.4, 7.1 Hz, 1H), 7.95 (d, 1H); MS (GC-MS) m/e 202 (M+H)⁺.

Compound 11. A mixture of compound 10 (2.5 g, 0.012 mol) and 10% Pd/C (2.5 g) in 20 mL of acetic acid is treated with hydrogen at about 50 psi overnight. The catalyst is filtered off and the solvent evaporated. The residue is partitioned between ethyl acetate (50 mL) and saturated NaHCO₃. The aqueous layer is extracted twice with ethyl acetate and the combined ethyl acetate layers are washed with brine, dried over Na₂SO₄, filtered and concentrated to give compound 11 (2.3 g, 100%) as an off-white solid: ¹H NMR (300 MHz, CDCl₃) 1.96–2.04 (m, 2H), 2.79 (t, J=6.3 Hz, 2H), 2.97 (t, J=6.0 Hz, 2H), 3.05 (t, J=8.7 Hz, 2H), 4.13 (t, J=8.7 Hz, 2H); MS (GC-MS) m/e 188 (M+H)⁺.

5-[(4–Chlorobenzyl)piperazin-1-yl]-1,2,4,5,6,7-hexahydro-4-oxo-pyrrolo-[3,2,1-jk][1]benzazepine, Compound 12

To a 0° C. solution of compound 11 (0.9 g, 4.8 mmol) in dichloromethane (9 mL) is added of N,N,N',N'-tetramethylethylenediamine (TMEDA) (2.10 mL) and trimethylsilyl iodide (2.00 mL). After about 30 min, solid iodine (1.8 g) is added and the reaction mixture is stirred at 0° C. for 40 min. A mixture of dichloromethane and excess aqueous sodium sulfite is added to quench the reaction. The reaction mixture is extracted several times with dichloromethane and the combined extracts are washed with brine, dried over Na₂SO₄, filtered and concentrated to give 1.40 g of crude product. An analytically pure sample can be prepared by chromatographing the crude product on silica gel, eluting with 25% ethyl acetate in hexanes. ¹H NMR (300 MHz, CDCl₃) 1.82–1.92 (m, 1H), 2.14–2.25 (m, 1H), 3.00–3.17 (m, 3H), 3.45–3.56 (m, 1H), 3.99–4.19 (m, 1H), 4.21–4.28 (m, 1H), 5.24 (d, J=6.6 Hz, 1H, ICH), 6.90–7.09 (m, 3H).

The above crude product, p-chlorobenzylpiperizine (0.63 g, 0.003 mol) and K₂CO₃ (0.3 g) are refluxed in acetonitrile (4 mL) for about 1 h. After cooling, the reaction mixture is filtered, concentrated and purified by chromatography on silica gel eluting with ethyl acetate followed by chloroform to yield compound 12 (1.1 g, 57% yield for two steps). ¹H NMR (300 MHz, CDCl₃) 1.99–2.08 (m,1H), 2.20–2.30 (m, 1H), 2.62 (bs, 4H), 2.82 (bs, 2H), 2.94–3.15 (m, 6H), 3.40 (d, J=8.5 Hz, 1H), 3.57 (s, 2H), 3.89–3.99 (m, 1H), 4.25–4.32 (m, 1H), 6.88–7.07 (m, 3H), 7.30–7.34 (m, 5H); MS (LC-MS) m/e 396 (M+H)⁺.

Example 2

The following compounds are prepared essentially according to the procedures set forth above in Example 1:

(a) 5-[(4-methylbenzyl)piperazin-1-yl]-1,2,4,5,6,7-hexahydro-4-oxo-pyrrolo-[3,2,1-jk][1]benzazepine (Compound 1). ¹H NMR (free base, 400 Hz, CDCl₃) δ 1.94–2.03 (m, 1H), 2.17–2.19 (m,1H), 2.33 (s, 3H), 2.56–2.71 (m, 6H), 2.95–3.17 (m, 6H), 3.35 (d, J=8.52 Hz, 1H), 3.47–3.55 (bs, 2H), 3.95–4.01 (m, 1H), 4.22–4.27 (m, 1H), 6.86–7.06 (m, 3H), 7.12 (d, J=7.69 Hz, 2H), 7.24 (d, J=7.96 Hz, 2H); MS (LC-MS) m/e 376 (M+H)⁺.

(b) 5-[(4-chlorobenzyl)piperazin-1-yl]-2,2-dimethyl-1,2,4,5,6,7-hexahydro-4-oxo-pyrrolo-[3,2,1-jk][1]benzazepine (Compound 2). MS (LC-MS) m/e 424 (M+H)⁺.

(c) cis-5-[(4-chlorobenzyl)piperazin-1-yl]-2-methyl-1,2,4,5,6,7-hexahydro-4-oxo-pyrrolo-[3, 2, 1-jk][1]benzazepine (Compound 4A).

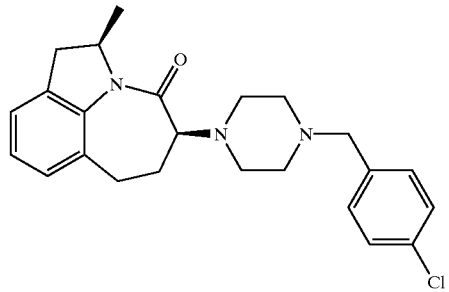

(d) trans-5-[(4-chlorobenzyl)piperazin-1-yl]-2-methyl-1,2,4,5,6,7-hexahydro-4-oxo-pyrrolo-[3,2,1-jk][1]benzazepine (Compound 4B).

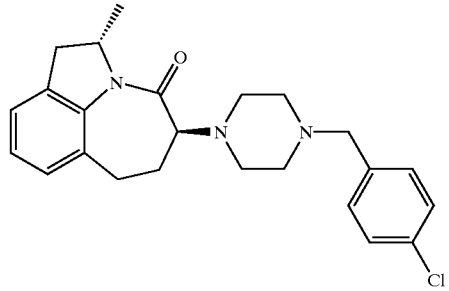

Compounds 4A and 4B are prepared as a diastereomeric mixture (identified herein as Compound 4) by condensation of 1-(4-chlorobenzyl)piperazine with diastereomeric 2-methyl-5-chloro-1,2,4,5,6,7-hexahydro-4-oxo-pyrrolo-[3,2,1-jk][1]benzazepine in the presence of base. The individual isomers may be separated by column chromatography.

(e) 5-[(2-methoxy-5-methylbenzyl)piperazin-1-yl]-2,2-dimethyl-1,2,4,5,6,7-hexahydro-4-oxo-pyrrolo-[3,2,1-jk][1]benzazepine(Compound 3). MS (LC-MS) m/e 434 (M+H)⁺.

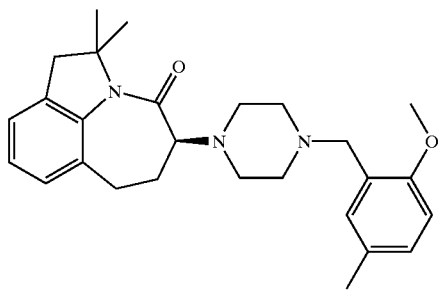

¹H NMR (CDCl₃) δ 7.16 (s, 1H), 6.9–7.0 (m, 4H), 6.74 (d, J=9 Hz, 1H), 3.77 (s, 3H), 3.54 (s, 2H), 3.25 (dd, J=9, 3 Hz, 1H), 2.8–3.0 (m, 6H), 2.67–2.71 (m, 2H), 2.53 (bs, 4H), 2.27 (s, 3H), 2.2 (m, 1H), 2.1 (m, 1H), 1.63 (s, 3H), 1.54 (s, 3H).

(f) 5-[(2-methoxy-5-chlorobenzyl)piperazin-1-yl]-2,2-dimethyl-1,2,4,5,6,7-hexahydro-4-oxo-pyrrolo-[3,2,1-jk][1]benzazepine(Compound 13).

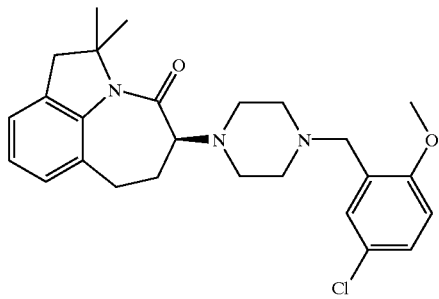

¹H NMR (CDCl₃) δ 7.36 (s, 1H), 7.15 (dd, J=9, 3 Hz, 1H), 6.9–7.0 (m, 3H), 6.75 (d, J=9 Hz, 1H), 3.78 (s, 3H), 3.52 (s, 2H), 3.25 (dd, J=9, 3 Hz, 1H), 2.8–3.0 (m, 6H), 2.69–2.74 (m, 2H), 2.52 (bs, 4H), 2.2 (m, 1H), 2.1 (m, 1H), 1.64 (s, 3H), 1.54 (s, 3H).

(g) 5-[(2-methoxy-4-methylbenzyl)piperazin-1-yl]-2,2-dimethyl-1,2,4,5,6,7-hexahydro-4-oxo-pyrrolo-[3,2,1-jk][1]benzazepine (Compound 14).

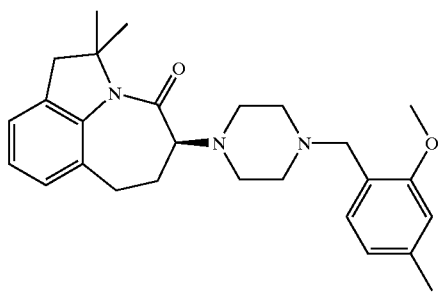

¹H NMR (CDCl₃) δ 7.19 (d, J=7 Hz, 1H), 6.8–7.0 (m, 3H), 6.71 (d, J=7 Hz, 1H), 6.66 (s, 1H), 3.78 (s, 3H), 3.51 (s, 2H), 3.22 (dd, J=9, 3 Hz, 1H), 2.8–3.0 (m, 6H), 2.61–2.67 (m, 2H), 2.5 (bs, 4H), 2.32 (s, 3H), 2.2 (m, 2H), 1.61 (s, 3H), 1.52 (s, 3H).

Example 3

Determination of D₂, D₄ and α₁ Receptor Binding Activity

The following assay is a standard assay for determining the binding affinity of compounds to dopamine $D_4$ and $D_2$ receptors.

Pellets of Chinese hamster ovary (CHO) cells containing recombinantly produced primate $D_2$, human $D_4$ and human α1 receptors are used for the assays. The sample is homogenized in 100 volumes (w/vol) of 0.05 M Tris HCl buffer containing 120 mM NaCl, 5 mM $MgCl_2$ and 1 mM EDTA at 4° C. and pH 7.4. The sample is then centrifuged at 30,000×g, resuspended and rehomogenized. The sample is then recentrifuged at 30,000×g, the supernatant is removed and the final tissue sample is frozen until it is needed. The tissue is resuspended 1:20 (wt/vol) in 0.05 M Tris HCl buffer containing 120 mM NaCl.

Incubations for dopaminergic binding are carried out at 25° C. and contain 0.4 ml of tissue sample, 0.1 nM ³H-YM 09151-2 (Nemonapride, cis-5–Chloro-2-methoxy-4-(methylamino)-N-(2-methyl-2-(phenylmethyl)-3-pyrrolidinyl)benzamide) and the compound of interest in a total incubation of 1.0 ml. Nonspecific binding is defined as that binding found in the presence of 1 μM spiperone; without further additions, nonspecific binding is less than 20% of total binding.

Norepinephrine al binding is carried out using ³H-prazosine as the ligand. Nonspecific binding is determined in the presence of 1 μM prazosine. Preferably, dopamine antagonists should not interact with the α1 adrenergic receptor, as interactions with this G-coupled protein receptor give rise to types of hypotension.

The binding characteristics of examples of this patent for the $D_2$, $D_4$ and α1 receptor subtypes are shown in Table 2.

TABLE 2

| Compound Number | $D_2$ $K_i$ (nM) | $D_4$ $K_i$ (nM) | α1 |
|---|---|---|---|
| 1 | 136 | 4 | 1095 |
| 2 | 201 | 19 | 1735 |
| 4 | 50 | 9 | >1 μM |

Preferred compounds of the invention exhibit Ki values of less than 500 nM at the dopamine $D_4$ receptor, more preferred compounds exhibit $K_i$ values of less than 100 nM and most preferred compounds of the invention exhibit $K_i$ values of less than 20 nM. Preferred compounds of the invention also exhibit greater than 20-fold selectivity for the dopamine $D_4$ receptor over the dopamine $D_2$ receptor; more preferred compounds of the invention exhibit greater than 100-fold selectivity for the dopamine $D_4$ receptor over the dopamine $D_2$ receptor.

Example 4

Preparation of Radiolabeled Probe Compounds of the Invention

The compounds of the invention may be prepared as radiolabeled probes by carrying out their synthesis using precursors comprising at least one atom that is a radioisotope. The radioisotope is preferably selected from of at least one of carbon (preferably ¹⁴C), hydrogen (preferably ³H), sulfur (preferably ³⁵S), or iodine (preferably ¹²⁵I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

Example 4a

Synthetic Scheme for the Preparation of the Radiolabled Compounds of the Invention

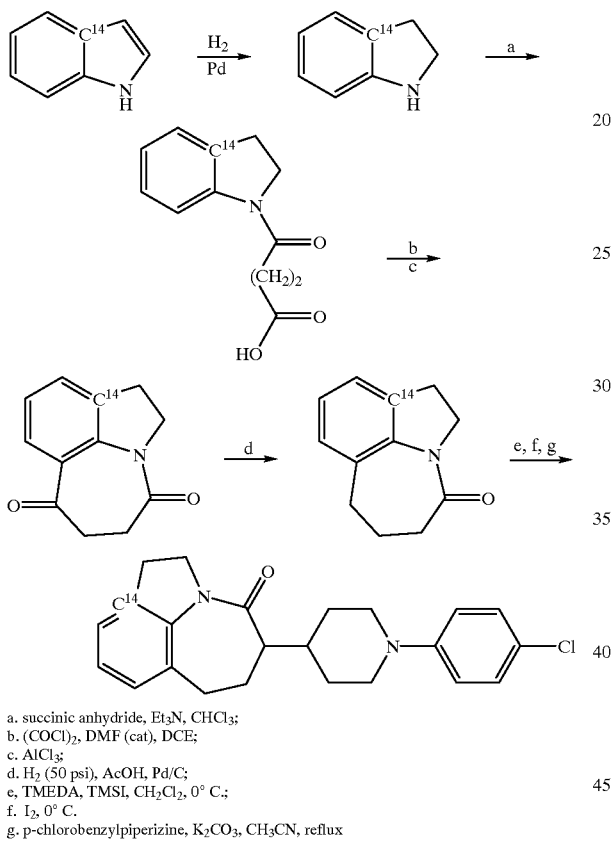

a. succinic anhydride, Et3N, CHCl3;
b. (COCl)2, DMF (cat), DCE;
c. AlCl3;
d. H2 (50 psi), AcOH, Pd/C;
e, TMEDA, TMSI, CH2Cl2, 0° C.;
f. I2, 0° C.
g. p-chlorobenzylpiperizine, K2CO3, CH3CN, reflux The above scheme, a modification of scheme I, represents a method for preparation of radiolabeled probe compounds of the invention. This synthesis is carried out using ARC-802 Indole, [2-$^{14}$C(U)], supplied by American Radiolabeled Chemicals, Inc., St. Louis, Mo., as the radioisotope precursor.

Example 5

Use of Compounds of the Invention as Probes for Dopamine Receptors in Cultured Cells and Tissue Samples Receptor autoradiography (receptor mapping) of NK-3 or GABA$_A$ receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which in it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

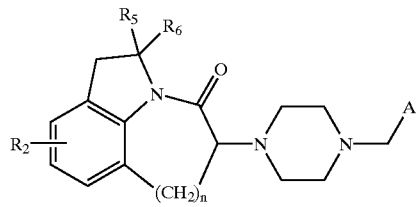

or a pharmaceutically acceptable salt thereof, wherein

A represents phenyl optionally substituted with up to four groups independently selected from halogen, hydroxy, amino, mono- or di($C_1$–$C_6$)hydrocarbylamino, aminosulfonyl, $C_1$–$C_6$ hydrocarbylaminosulfonyl, di($C_1$–$C_6$)hydrocarbylaminosulfonyl, cyano, nitro, cyclohydrocarbylhydrocarbyl, trifluoromethyl, $C_1$–$C_6$ hydrocarbyl, trifluoromethoxy, $C_3$–$C_6$ cyclohydrocarbyl, and $C_1$–$C_6$ alkoxy;

$R_5$ and $R_6$ are the same or different and represent hydrogen or $C_1$–$C_6$ hydrocarbyl; and $R_2$ represents hydrogen, halogen, hydroxy, amino, mono- or di($C_1$–$C_6$)hydrocarbylamino, aminosulfonyl, $C_1$–$C_6$ hydrocarbylaminosulfonyl, di($C_1$–$C_6$) hydrocarbylaminosulfonyl, cyano, nitro, cyclohydrocarbylhydrocarbyl, trifluoromethyl, $C_1$–$C_6$ hydrocarbyl, trifluoromethoxy, $C_3$–$C_6$ cyclohydrocarbyl, or $C_1$–$C_6$ alkoxy; and n is 0 or 1.

2. A compound according to claim 1, wherein $R_2$ is hydrogen, fluoro, chloro, or $C_1$–$C_2$ alkyl.

3. A compound according to claim 2 wherein A is a group of the formula:

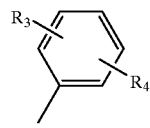

where $R_3$ and $R_4$ independently represent hydrogen, halogen, hydroxy, amino, mono- or di($C_1$–$C_6$)alkylamino, aminosulfonyl, $C_1$–$C_6$ alkylaminosulfonyl, di($C_1$–$C_6$) alkylaminosulfonyl, cyano, nitro, cycloalkylalkyl, trifluoromethyl, $C_1$–$C_6$ alkyl, trifluoromethoxy, $C_3$–$C_6$, cycloalkyl, or $C_1$–$C_6$ alkoxy.

4. A compound according to claim 3, wherein at least one of $R_3$ and $R_4$ is in the ortho or para position of the phenyl ring.

5. A pharmaceutical composition comprising a compound according to claim 1, together with at least one pharmaceutically acceptable carrier or excipient.

6. "A method for the treatment of schizophrenia comprising administering to a patient in need of such treatment a therapeutically effective amount of a compound of claim 1."

7. "A method for the treatment of Parkinson's disease comprising administering to a patient in need of such treatment a therapeutically effective amount of a compound of claim 1."

8. "A method for the treatment of psychotic depression comprising administering to a patient in need of such treatment a therapeutically effective amount of a compound of claim 1."

9. "A method for the treatment of mania comprising administering to a patient in need of such treatment a therapeutically effective amount of a compound of claim 1."

10. "A method for the treatment of tardive dyskinesia comprising administering to a patient in need of such treatment a therapeutically effective amount of a compound of claim 1."

* * * * *